United States Patent [19]

Snyder et al.

[11] Patent Number: 5,128,246
[45] Date of Patent: Jul. 7, 1992

[54] METHODS FOR ISOLATING AND EXPRESSING GENE FOR ODORANT BINDING PROTEIN

[75] Inventors: Solomon H. Snyder; Jonathan Pevsner; Randall Reed, all of Baltimore, Md.

[73] Assignee: The Johns Hopkins University, Baltimore, Md.

[21] Appl. No.: 492,792

[22] Filed: Mar. 13, 1990

Related U.S. Application Data

[62] Division of Ser. No. 175,180, Mar. 30, 1988, Pat. No. 5,030,722.

[51] Int. Cl.$^5$ .................. C12N 15/12; G12P 21/02
[52] U.S. Cl. .................. 435/69.1; 435/172.3; 935/4
[58] Field of Search .................. 435/69.1, 172.3; 530/350, 412; 935/4

[56] References Cited

U.S. PATENT DOCUMENTS 4,769,326  9/1988  Rutter .................. 435/68

OTHER PUBLICATIONS

P.N.A.S. 78:6613-6617, Nov. 1981, Suggs et al., Use of Synthetic Oligonucleotides as Hybridization Probes: Isolation of Cloned cDNA Sequences for Human $B_2$-Microglobin.
P.N.A.S. 82:3050-3054, May 1985, Pevsner et al., Isolation and Characterization of an Olfactory Receptor Protein for Odorant Pyrazines.
Nature 313:806-810, Feb. 1985, Jacobs et al., Isolation and Characterization of Genomic and cDNA Clones of Human Erythropoietin.
Science 222:778-782, Nov. 18, 1983, Young et al., Yeast RNA Polymerase II Genes: Isolation with Antibody Probes.
Pevsner et al., PNAS, vol. 83, pp. 4942-4946, 1986.
Cavaggioni, FEBS Letters, vol. 212, pp. 225-228, 1987.
Bignetti, European Journal of Biochemistry, vol. 149, pp. 227-231, 1985.
Lee, Science, vol. 235, pp. 1053-1056, 1987.
Pace, Nature, vol. 316, pp. 255-258, 1985.
Rogers, PNAS. vol. 84, pp. 1704-1708, 1987.
Sklar, J. Biol. Chem., vol. 261, pp. 15538-15543, 1986.

Primary Examiner—Richard A. Schwartz
Assistant Examiner—John D. Ulm
Attorney, Agent, or Firm—Banner, Birch, McKie & Beckett

[57] ABSTRACT

DNA molecules are taught which code for an odorant-binding protein which is synthesized solely in the lateral nasal gland. This protein, because of the broad range of odorants which it binds, can be used in many techniques for trapping odorants in either a liquid or solid medium. This protein bears some structural homology with other carriers of small lipophilic molecules from many other species; the carriers are known to transport specific lipophilic molecules.

6 Claims, 9 Drawing Sheets

FIG. 1A

```
1    G AAT CCA GGC TCT AAC ATG GTG
                             MET Val

74   AAT CTT GAT ATC AGT CCC TCA GAG
     Asn Leu Asp Ile Ser Pro Ser Glu

Bam HI
149  GTA GCA GAA GGT GGA TCC CTG AGA
     Val Ala Glu Gly Gly Ser Leu Arg

224  ATA TTC AAT GTC AAG TTG GAC AGT
     Ile Phe Asn Val Lys Leu Asp Ser

299  ACT ACT GAC TAC TCT GGT AGA AAT
     Thr Thr Asp Tyr Ser Gly Arg Asn

Taq I
374  AAT GTC GAT GAG AGT GGA AGG AGA
     Asn Val Asp Glu Ser Gly Arg Arg

449  CAG GAG CTT AGG AAG CTG GCT GAG
     Gln Glu Leu Arg Lys Leu Ala Glu

A*
524  TGT AAC CAA TAA AGA CTC CAT ATG
     Cys Asn Gln stop

599  TGA AAT CAG AAT CGT GAC AAT GAA

674  AAA ATC TGC TTC GTG GAT TTG TTT

749  TTT CAT GCA CAA AAA AAA AAA AAA
```

*Clone 800

FIG. 1B

```
AAG TTT CTG CTG ATT GTT CTT GCA TTA
Lys Phe Leu Leu Ile Val Leu Ala Leu

GTT AAT GGG GAC TGG CGC ACC CTT TAC
Val Asn Gly Asp Trp Arg Thr Leu Tyr

GCT TAC TTT CAG CAC ATG GAA TGT GGT
Ala Tyr Phe Gln His Met Glu Cys Gly

GAA TGT CAG ACA CAC ACT GTT GTG GGA
Glu Cys Gln Thr His Thr Val Val Gly

TAC TTC CAT GTT TTG AAG AAG ACA GAT
Tyr Phe His Val Leu Lys Lys Thr Asp

CAA TGT GAT TTA GTT GCT GGG AAA AGA
Gln Cys Asp Leu Val Ala Gly Lys Arg

GAG TAT AAT ATT CCA AAT GAG AAT ACC
Glu Tyr Asn Ile Pro Asn Glu Asn Thr

HncII A*
GCT TCA CAA AGG ACA GCA AGG TCA GCA

GAT AAC TCA TCC TTT TCT TAT TTT TTC

CCC ACC CTC CTA TCA TGG TAC TGA TTC

AAA AAA AAA AAA AAA AAA AAA AAA AAA
```

FIG. 1C

```
GGT GTA TCC TGT GCA CAT CAT GAA
Gly Val Ser Cys Ala His His Glu   19

ATA GTT GCA GAT AAT GTG GAG AAG
Ile Val Ala Asp Asn Val Glu Lys   44

GAT GAA TGC CAG GAA CTC AAA ATC
Asp Glu Cys Gln Glu Leu Lys Ile   69

CAA AAA CAT GAA GAT GGG CGG TAC
Gln Lys His Glu Asp Gly Arg Tyr   94

GAC ATT ATT TTC TTT CAC AAC GTT
Asp Ile Ile Phe Phe His Asn Val  119

GAG GAC CTG AAC AAA GCA CAG AAG
Glu Asp Leu Asn Lys Ala Gln Lys  144

CAG CAC TTG GTG CCC ACA GAC ACT
Gln His Leu Val Pro Thr Asp Thr  169

ATA TTT CCC ACA TCA CCT TTT CCA

TTT TCA TCT TTC CTA TGA AGC CAG
                                G*
TTC TGT TGA TAA AAT AAA TTT ATT

AA 801
```

FIG. 3A  FIG. 3B
1  2  3  4
23.1 ➤
9.4 ➤
6.6 ➤
4.4 ➤
2.3 ➤
2.0 ➤
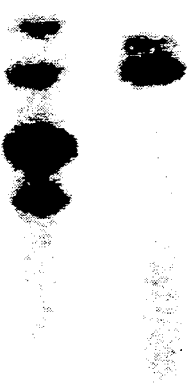
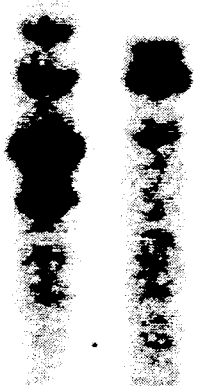

FIG. 4

```
OBP                            MVKFLLIVLALGVSCAHHENLDISPS   26
A2G                           LLLLCLGLTLV-CGHAEEASSTRGNLDVA
BBLG                                       LIVTQTMKGLDIQ
BG                                      QC-QADLPPVKKG-LECN
HC                                     GPVPTPPDNIQVQENFNIS
APOD   MVMLLLLLSALAGLFGAAEGCAFHLGKCPNPPVQENFDVN
THI                        GDIFYPGYCPDVKPVNDFDLS
RBP             MKWVWALLLLAAWAAAERDC-RVS-SFRVKENFDKA
PURP       MKYAQYVFLASIFSAVEYSLAQTC-AV-DSFSVKDNFDPK
AGP            HALHMVLVVLSLLPLLEAQNPEPANITLGIPITNETLK

OBP     EYNGDWRTLYIVAD-NVEK--YA-EGGSLRAY-FQHMECG   61
A2G     KINGDWFSTVVASN-KREK--IE-ENGSMRVF-HQHIDVL
BBLG    KVAGTWYSLAMAAS-DISL--LDAQSAPLRVY-VEELKPT
BG      KYTGVWYGIAAASN-CKQF--LQMKSDNMPAP-VNIYSLN
HC      RIYGKWYNLAIGSTCP-LK--IM-DRMTVSTL-VLGEGAT
APOD    KYLGRWYEIEKIPTTFENGRCLQA-NYSL--HENGKIKVL
·THI    AFAGAWHELAKLPL-ENEN--LQ-GKCTIAEY-KYDGKKA
RBP     RFSGTWYAMA-KKD-PEGL--FL-QDNIVAEFSVDETGQM
PURP    RYAGKWYALA-KKD-PEGL--FL-QDNISAEYTVEEDGTM
AGP     WLSDKWFYMGAAFRDPVFK--QA-VQTIQTEF-FYLTP--

OBP     -DECQELKIIFNVKLD-SECQTHTVVGQ-K-HEDGRY-T-   95
A2G     -ENSLGFK--FRIKEN-GECRELYLVAY-KTPEDGEY-F-
BBLG    PEGDLEIL--LQKWEN-GECAQKKIIAE-KTKIPAVF-K-
BG      -NGHHKSS--TSFQTE-KGCQOMD-VEM-TTVEKCHYKW-
HC      -EAEISHT--STRWRK-GVCEETS-GAYEKTDTDGKFLYH
APOD    -NQELRAD--GTVNQIEGEATPVNLTEPAK--LEVKY---
THI     -SVYNSFV-SNGVKEY-MEG-DLEIAPDAKYTKQFKY-V-
RBP     -SATAKGR--VRLLNNWDVCADM-VGTFTDTEDPAKF-KM
PURP    -TASSKGR--VKLFGFWVICADMAAQYTVPDPTTPAKMYM
AGP     -NLINDTIELREFQTTDDQCVYNFTHLG-VQRENGTL-S-

OBP     -TDYS-GR-NY----THVLKKT-DDITF-FH-NVNV-DES   124
A2G     -VEYD-GG-NT----ETILKTSYDRYVH-FH-LINF-KNG
BBLG    -IDAL-NE-NK----VLVLDTDYKKYLL-FC-MENS-AEP
BG      -KMQQ-GD-SE----TIIVATDYDAFLM-EF-TKIQ-M-G
HC      KSKWN-ITMES----V-VVHTNYDEYAI-FL-TKKF-SRH
APOD    -SWFM-PS-AP----YWILATDYENYAL-VY-SCTC-IIQ
THI     -MTFKFGQRVVNL-VPWKLATDYKNYALNYNCDYHPDKKA
RBP     KYWGVASFLQKGNDDHWIVDTDYDTYAVQY-SCRLLN-LD
PURP    TYQGLASYLSSGGDNYWVIDTDYDNYAITY-ACRSLK-ED
AGP     -KCA--GAVKI----FAHLIVLKKHGTF-HL-AFNL-TDE

OBP     G-RRQCDL-VAGKREDLNKAQKQE-RKLAEEYNIPNENTO   162
A2G     E-TFQLMV-LYGRTKDLSSDIKEKFAKLCEAHGITRDNII
BBLG    EQSLACOC-L-VRTPEVDDEALEKFDKALKALPMHIRLSF
BG      A-EVCVTVKLFGRKDTLPEDKIKHFEDHIEKVGLKKEQYI
HC      H-GPTITAKLYGRAPQLRETLLQDFRVVAOGVGFPEDSIF
APOD    -LFHVDFAWILARNANLPPETVDSLKNILTSNNIDVKKMT
THI     H-SIHAWI-L-SKSKVLEGNTKEVVDNVLKTFSHLIDASK
RBP     GTCADSYSFVFSRDPNGLPPEAQKIVRQRQEELCLARQYR
PURP    GSCDDGYSLIFSRNPRGLPPAIQRIVRQKQEEICMSGQFQ
AGP     ---NRGLS-IYAKKPDLSPELRKIFQQAVKDVGMDESEIV
```

FIG. 4 (cont.)

```
OBP    HLVPTDT-CNQ    172
A2G    DLTKTDR-CLOARG
BBLG   NRTQLEEQCHI
BG     RFHTKAT-CVPK
HC     THADRGE-CVPGEQEPEPILIPR
APOD   -VTDQVN-CPKLS
THI    FISNDFSEAACQYSTTYSLTGPDRH
RBP    LIVHNGY-CDGRSERNLL
PURP   PVLCSGA-C
AGP    FVDWTKDKCSEQKQQLELEKETKKETKKDP
```

FIG. 5A  FIG. 5B
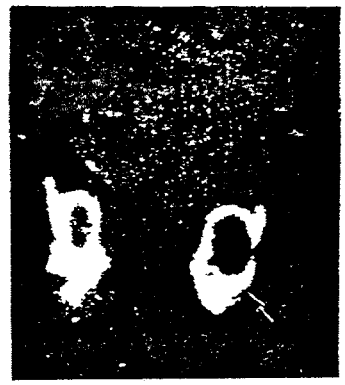 
FIG. 5C  FIG. 5D
 
FIG. 5E  FIG. 5F
 

METHODS FOR ISOLATING AND EXPRESSING GENE FOR ODORANT BINDING PROTEIN

This work was partially supported by grants from the United States Department of Health and Human Services. The United States Government may retain certain rights in this invention.

This application is a division, of application Ser. No. 175,180, filed Mar. 30, 1988, now U.S. Pat. No. 5,030,722.

TECHNICAL FIELD OF THE INVENTION

This invention relates to the area of olfactory perception. More specifically it relates to the initial steps in the process of olfactory perception.

BACKGROUND OF THE INVENTION

The complete molecular mechanism responsible for olfaction has yet to be elucidated. However, odorant binding activity has been detected in mammalian olfactory tissue extracts. In addition, behavioral and neurophysiological evidence suggests the existence of specific olfactory receptor proteins. For example, Amoore reports losses of the sense of smell (anosmias) to about thirty discrete odorant groups. (Chem. Senses Flavor, Vol. 2, pp. 267-281, 1977.) In addition, there is evidence for a binding protein for urinous odorants (Persaud et al, in *Biochemistry of Taste and Olfaction* (1981), Cagan et al, editors, pp. 333-357, Academic Press, New York), a camphor-binding protein (Fesenko et al, Biochim. Biophys. Acta, Vol. 587, pp. 424-433, 1979) and a binding protein for green smelling odorants such as 2-isobutyl-3-methoxyprazine (IBMP) (Pelosi et al, Biochemical Journal, Vol. 201, pp. 245-248, 1982). Despite these findings, the molecular identity of most of the components of the olfactory system remain undefined.

At the molecular level, several proteins have been identified which appear to be involved in olfaction. Lee et al, Science, Vol. 235, pp. 1053-1956 (1987) report the isolation of an olfactory cDNA from the frog. The mRNA corresponding to the isolated cDNA appears to be abundant in the Bowman's glands in olfactory tissue, but not in other tissues tested. Although the function of the protein encoded by the gene is unknown, its sequence shares homology with members of a family of proteins that bind and transport small molecules in the serum, suggesting a transporting role for this protein.

Another protein presumably involved in olfaction is the so-called pyrazine-binding protein or odorant-binding protein from cow nasal tissue. This protein was first detected on the basis of its binding activity for "green" smelling compounds such as 2-isobutyl-3-methoxypyrazine. (See Bignetti et al, European Journal of Biochemistry, Vol. 149, pp. 227-231, 1985 and Pevsner et al, Proceedings of the National Academy of Sciences, Vol. 82, pp. 3050-3054, 1985.) This cow protein has been purified to apparent homogeneity and a partial amino acid sequence has been determined (See Cavaggioni et al, FEBS Letters, Vol. 212, pp. 225-228, 1987). Homology between this cow protein and the major mouse urinary proteins (MUP) and the rat alpha-2-microglobulins (AMG) was noted.

A rat odorant-binding protein has also been purified to apparent homogeneity. (Pevsner et al, Proceedings of the National Academy of Sciences U.S.A., Vol. 83, pp. 4942-4946, 1986.) The protein was found in both olfactory and respiratory epithelium. Although it was known that the rat odorant protein was secreted into the nasal mucus and tears, it was not known where this protein was synthesized.

Another identified protein which is presumably involved in olfaction is the so-called olfactory marker protein (OMP). This is a neuronal gene product which is developmentally regulated and whose expression is restricted to mature olfactory receptor neurons of many vertebrate species. The gene for this protein has been cloned and sequenced. (See Rogers et al, Proceedings of the National Academy of Sciences U.S.A., Vol. 84, pp. 1704-1708, 1987.) Another protein which has been identified in the olfactory perception system is an odorant-sensitive adenylate cyclase. This was found in olfactory sensory neurons and requires the presence of guanosine triphosphate (GTP). Only certain odorants are found to stimulate the enzyme activity. (See Journal of Biological Chemistry, Vol. 61, pp. 15538-15543, 1986.)

There is a need for a more thorough understanding of the components of the olfactory perception system. Molecular cloning of these components can facilitate the understanding of the mechanism of olfaction by allowing the production of large amounts of the individual components. Further, molecular cloning can facilitate the determination of the sites of synthesis of various components of the olfactory system.

Because odorant molecules are often present in rather small amounts in natural sources, they can be difficult to isolate and/or analyze. Thus there is a need for a large source of an odorant binder to facilitate the isolation and identification of odorant molecules. Further, some odorant molecules are readily absorbed into the skin which can both be deleterious to the health and cause the odorant (for example, a perfume) to have a short active life on the skin. Therefore there is a need in the art for compounds which can extend the active life of odorants on the skin. In addition, many odorants are lipophilic, and thus are difficult to bring into aqueous or semi-aqueous solution. Thus there is a need in the art for compounds which can facilitate the emulsification of lipophilic odorant molecules.

SUMMARY OF THE INVENTION

It is an object of the present invention to provide a method of isolating an odorant-binding protein gene.

It is another object of the invention to provide a method of producing an odorant-binding protein.

It is yet another object of the invention to provide a DNA molecule which encodes an odorant-binding protein.

It is another object of the invention to provide a method of concentrating odorants on a solid support.

It is another object of the present invention to provide a method of reducing the rate of volatilization of odorants from solutions.

It is yet another object of the present invention to provide a method of solubilizing lipophilic odorants in aqueous media.

It is still another object of the present invention to provide a method of screening for potent odorants in crude extracts of natural tissues.

These and other objects are fulfilled by the present invention in one or more of the embodiments described below. In one embodiment of the present invention, a method is provided for isolating an odorant-binding protein gene, comprising: preparing cDNA using mRNA templates isolated from lateral nasal gland tissue; inserting the cDNA into DNA vectors to form recombinant DNA molecules; transforming host cells with said recombinant DNA molecules to form transformed cells; and detecting the presence of odorant-binding protein DNA in said transformed cells.

In another embodiment of the invention a method is provided for producing an odorant-binding protein, comprising: transforming host cells with a recombinant DNA molecule comprising an odorant-binding protein gene which is positioned downstream from a transcriptional promoter and downstream from and in phase with a translational start site to form transformed cells; growing said transformed cells in a culture medium under conditions such that said transformed cells express the protein encoded by said odorant-binding protein gene; and harvesting the expressed protein encoded by said odorant-binding protein gene from said transformed cells and/or said growth medium.

In yet another embodiment of the invention a DNA molecule is provided which is free of introns and which encodes a protein having a sequence corresponding to that shown in FIG. 1 for the rat odorant-binding protein. The rat odorant-binding protein has been discovered to be synthesized in the lateral nasal glands (LNG). Such odorant-binding proteins which are produced in the LNG are termed herein $OBP_L$.

In yet another embodiment of the present invention a method is provided of concentrating odorants on a solid support, comprising: applying an $OBP_L$ to a solid support, and contacting said solid support with odorant compounds to effect binding of the odorant to said solid support via $OBP_L$.

In yet another embodiment of the present invention a method is provided of reducing the rate of volatilization of odorants from solutions, comprising: providing a solution containing a volatile odorant, and mixing a volatilization-reducing amount of $OBP_L$ with said solution.

In still another embodiment of the present invention a method is provided of solubilizing lipophilic odorants in aqueous media, comprising: providing an aqueous medium; binding a liphophilic odorant to $OBP_L$, and mixing said $OBP_L$-bound lipophilic odorant with the aqueous medium to form an aqueous perfumed product.

In yet another embodiment of the present invention a method is provided of screening for potent odorants in crude extracts of natural tissues, comprising: binding a strong odorant to $OBP_L$ to form a bound $OBP_L$ and strong odorant complex; making an extract of a natural tissue; making serial dilutions of the extract; and determining which dilutions of the extract are able to displace the bound, strong odorant from the complex, an extract which can displace the strong odorant at a high dilution indicating the presence of a potent odorant in the natural tissue.

BRIEF DESCRIPTION OF THE DRAWINGS

FIGS. 1A–C show the nucleotide sequence and predicted amino acid sequence of three cDNA clones of rat $OBP_L$.

FIGS. 3A–B show a Southern blot analysis of genomic DNA from rat liver using an $OBP_L$ probe.

FIG. 4 shows the amino acid sequence alignments of $OBP_L$ and ten homologous proteins.

FIGS. 5A–F show the in situ hybridization of labeled cRNA for $OBP_L$ as well as immunohistochemical staining with anti-$OBP_L$ antiserum and autoradiography using tritiated odorants.

DETAILED DESCRIPTION OF THE INVENTION

Figure 2:
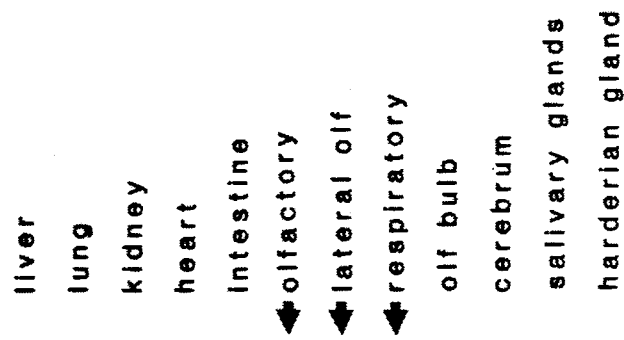
FIG. 2 shows a Northern blot analysis of the distribution of $OBP_L$ message and OMP message in various tissues.

It is a discovery of the present invention that odorant-binding protein in the rat is synthesized in the lateral nasal gland. The rat has between fifteen and twenty discrete nasal glands. The lateral nasal gland is one which does not exist in the cow, but does exist in other mammals, such as the human.

Before the work of the present invention, the site of synthesis of odorant-binding protein in the rat was unknown. Odorant binding protein itself, as well as odorant binding activity, had been found in rat mucus and tears, as well as in the olfactory epithelium. Much less activity was found in the respiratory epithelium. In the cow, odorant-binding protein had been found immunohistochemically in the glands of the lamina propria and along the surface of the epithelium; it was found in both olfactory and respiratory glands.

It has now been discovered that the presence of $OBP_L$ in the epithelium and mucus of rats is due to secretion from its site of synthesis in the lateral nasal gland. It would have been extremely difficult, if not impossible, to isolate the mRNA encoding OBP from these epithelial tissues in rats. Although not wishing to be bound by any particular theory, applicants believe that it is only because they have used tissue preparations containing the lateral nasal gland to make their cDNA library, that they were able to isolate the OBP cDNA.

It has been found that the $OBP_L$ gene is a member of a larger family of proteins which have ligand carrier properties. Table 1, below, shows the physical properties of the ligand-binding carrier family. The family membership of $OBP_L$ has been recognized by use of computer comparison of amino acid sequences. All of the proteins in this family have a similar subunit molecular weight. Many of them bind and serve as carriers for small lipophilic molecules, while the function of some is yet undetermined.

Insecticyanin binds the small lipophilic molecule biliverdin IX. Apolipoprotein D binds cholesterol and cholesteryl esters and has been proposed as a carrier for chloesterol. One of the best characterized of these proteins is retinol binding protein. It serves as a carrier for retinol, transferring retinol from plasma to the pigmented epithelium of the retina.

One of the consensus sequences recognized among this family of proteins also occurs near the N-terminus of a different family of ligand-binding proteins of which retinol-binding protein is a member. Other members of this family include cellular retinol binding protein I and II, cellular retinoic acid binding protein, peripheral nerve myelin P2 protein, heart and intestinal fatty acid binding protein, and murine adipocyte protein P422.

While the inventors do not wish to be bound by any particular theory, it is proposed that $OBP_L$ functions in an analogous fashion to retinol binding protein. Lipophilic odorants could more readily traverse the hydrophilic environment of the nasal passages to reach the odorant receptors on the cilia of olfactory neurons if bound to $OBP_L$. $OBP_L$ might also facilitate the transfer of odorants to the receptors which are bathed in hydrophilic mucus.

According to the method of the present invention, an odorant-binding protein gene is isolated by preparing cDNA from mRNA which has been isolated from lateral nasal gland tissue. Since the lateral nasal gland is the sole site of expression of the odorant-binding protein RNA, it is beneficial that the tissue preparation contain predominantly lateral nasal gland cells. The lateral nasal gland is one of the largest of the nasal glands. See Bojsen-Moller, Anat. Rec., Vol. 150, pp. 11-24, 1964, and Cuschiere et al., Histochemical Journal Vol. 6, pages 543-558, 1974. The lateral nasal gland (LNG) is located in the posterior area of the nose, just ventral and anterior to the olfactory epithelium on the lateral wall. Its main excretory duct is long and extends anteriorly, opening into the internal ostium at the tip of the nose. Contamination of the lateral nasal gland tissue preparation with other tissues will reduce the frequency of $OBP_L$ clones in the cDNA library isolated.

Messenger RNA can be isolated from lateral nasal gland tissue according to methods well known in the art. Briefly, RNA can be purified by affinity chromotography on oligo(dT) cellulose to separate the poly-(A)-containing mRNA from other RNAs. Methods for (1) isolation of mRNA from mammalian cells, (2) selection of poly(A) RNA and (3) cDNA synthesis using mRNA as a template, can be found in Maniatis, et al. *Molecular Cloning: A Laboratory Manual*, Cold Spring Harbor Labs, 1982.

The cDNA which has been prepared can be inserted into appropriate DNA vectors to form recombinant DNA molecules. Many methods are well known in the art for accomplishing this, for example, adding complementary homopolymer tracts to double-stranded cDNA and to the vector DNA. The vector and double-stranded cDNA are then joined by hydrogen binding between the complementary homopolymeric tails. In vitro enzymatic ligation is not necessary to establish these recombinant vectors in *E. coli*. Alternatively, synthetic linkers can be added to the termini of the double-stranded cDNA. After cleavage with the appropriate restriction enzyme, the cDNA molecules are inserted into plasmid DNA that has been cleaved with a compatible enzyme. Again, such methods are well known in the art. See Maniatis, supra.

Suitable host cells can be transformed according to known methods in the art to achieve uptake by the cells and stable replication of the recombinant DNA molecules. The cells may be of prokaryotic or eukaryotic derivation. Choice of suitable host cells and vectors is well within the skill of the art. *E. coli* is a common choice.

In order to isolate the transformed cells which contain a molecular DNA clone of the odorant-binding protein, a detection means must be employed. Again, choice of a detection means is well within the skill of the art, although a few means will be specifically mentioned below. In one detection method, a nucleic acid probe is used which comprises a mixture of sequences, each of which codes for a portion of the amino acid sequence of the the odorant-binding protein. That is to say that the probe contains all of the possible coding sequences for a sequence of amino acids of odorant-binding protein. This method was used by the present inventors to construct a mixed oligonucleotide probe (21 mer) containing thirty-two distinct molecular species. These probes were constructed based on the frequency of codon utilization. See Lathe et al, Journal of Molecular Biology, Vol. 183, p. 1, 1985.

In another method for detecting odorant-binding protein genes, a nucleic acid probe is utilized which comprises at least about twenty nucleotides from the DNA sequence determined for rat odorant-binding protein. Thus the information gained from the rat odorant-binding protein gene can be used to isolate $OBP_L$ genes from other mammalian organisms containing lateral nasal glands. Similarly, when $OBP_L$ genes are isolated from other mammals, those sequences can be used to construct probes to still other mammalian species. In still another method for detecting cloned genes, cross-reacting material produced by the transformed cells is tested. That is to say that the products of transformed cells can be screened with antiserum which contains antibody reactive with odorant-binding protein of the rat. In cases where one has inserted the $OBP_L$ DNA in a vector such that a fusion protein will be synthesized, or where full or partial length $OBP_L$ gene expression is expected, this immunological method can be used. Methods for immunological as well as hybridization testing of recombinant clones are well known in the art.

In another detection method which can be used when cDNA has been inserted into DNA vectors such that expression can be expected, the transformed cells can be screened for the production of a protein which specifically binds odorant molecules. For example, binding of tritiated 2-isobutyl-3-methoxypyrazine (IBMP) can be used as an assay to identify transformed cells which bind IBMP, presumably by expressing an odorant-binding protein. See, for example, Pevsner et al., Proceeding of the National Academy of Sciences U.S.A., Vol. 82 pp. 3050-3054, 1985.

Odorant binding protein can be made using host cells which have been transformed with recombinant molecules. The recombinant molecules have odorant-binding protein genes positioned downstream from a transcriptional promoter and downstream from and in phase with a translational start site. Suitable vectors and methods for constructing such recombinant molecules are well known in the art. Once such recombinant molecules and transformed cells have been produced, they can be grown in a culture medium under conditions such that the protein encoded by the odorant-binding protein gene is expressed. For example, if the odorant-binding protein gene is under the control of an *E. coli* lac promoter and operator, expression of the odorant-binding protein gene can be induced using isopropyl-beta-D-thiogalactoside.

The protein may be expressed as either the full-length odorant-binding protein, a portion thereof, or as a fusion protein with a portion of another protein covalently attached. Depending on the particular construction of the recombinant molecule, the protein which is produced may be harvested either from the growth medium (if the protein is secreted), or from the transformed cells themselves. Suitable methods for harvesting and isolating proteins from transformed cells and growth media are well known in the art.

DNA molecules which are contemplated and embraced by the present invention include those which are free of introns, because they have been isolated via mRNA, as discussed above. These cDNA molecules will have sequences which correspond to that shown in FIG. 1 for rat $OBP_L$. While this protein shares about 30% identity with other members of the family of lipophilic molecule carrier proteins, it also shares that amount of identity with pyrazine-binding protein isolated from the cow, (also called odorant-binding protein.) Thus $OBP_L$ isolated from the rat is no more similar to the pyrazine-binding protein of cow than it is to rat alpha-2-micro-globulin or to rat major urinary protein. Nonetheless, it is expected that odorant-binding proteins similar to $OBP_L$ will be found in other mammalian species, especially those of mammals having a lateral nasal gland. These homologous proteins would be expected to have substantial homology with $OBP_L$, at least greater than about 50%, and preferably greater than about 75%.

While the overall protein structures of the $OBP_L$ family members (as determined by X-ray crystallography) are remarkably similar, none of the amino acids in the consensus sequences is in contact with the bound ligand. Thus, although applicants do not wish to be bound by any particular theory regarding the mechanism of action of $OBP_L$, it is quite possible that odorants are bound by $OBP_L$ merely on the basis of their overall size, conformation, and hydrophobicity. This is consistent with the extremely catholic binding abilities found for $OBP_L$. For example, $OBP_L$ will bind 2-isobutyl-3-methoxypyrazine, methyldihydrojasmonate, as well as 3,7-dimethyloctan-1-ol. Because of this extremely broad range of odorant binding, $OBP_L$ can be used for many different purposes.

In one method of use, $OBP_L$ is used to concentrate odorants on a solid support. $OBP_L$ can be covalently attached to the solid support or can be noncovalently attached, for example merely admixed or in intimate contact with the solid support such that the combination of $OBP_L$ and solid support is stable. Solid supports include human skin, agarose beads, cellulose, or other inert solids. In one such proposed method, the solid support is a human nose. If $OBP_L$ is applied to the exterior portions of the nose only, odorants will be concentrated outside of the nose and their diffusion into the nose to the olfactory perception system will be greatly reduced. Since the sense of taste and appetite are known to be enhanced by perception of certain odorants, such a method could be used to reduce the appetite of obese humans. Conversely, if $OBP_L$ were applied to the interior portions of the nose, for example, those portions bathed in mucus, odorants would be concentrated to the mucus and this would enhance the amount of odorant perceived by the human. This can be useful in situations where appetite has been depressed either by illness or chemotherapy. Further, applicants have also found that when $OBP_L$ is mixed with odorants, the odorant stimulation of the enzyme odorant-sensitive adenylate cyclase is enhanced relative to the stimulation in the absence of $OBP_L$. Thus $OBP_L$ would both concentrate odorants and enhance their perception.

In still another method of use, $OBP_L$ protein is applied to human skin before or concomitantly with a perfume or perfumed product. By trapping the odorant of the perfume at the skin, $OBP_L$ can decrease the amount of such odorants absorbed by the skin. This would be beneficial in situations where it is not desirable that the odorants be absorbed into the skin; also it would prolong the useful time period of the perfume on the body.

The term perfume is used herein to mean a mixture of organic compounds including, for example, alcohols, aldehydes, ketones, nitriles, ethers, lactones, acetals, esters, and frequently hydrocarbons which are admixed so that the combined odors of the individual components produce a pleasant or desired fragrance. Also included here are natural and synthetic "essential oils". Such perfumes usually contain: (a) the main note or the "bouquet" or foundation-stone of the composition; (b) modifiers which round-off and accompany the main note; (c) fixatives which include odorous substances which lend a particular note to the perfume throughout all stages of evaporation, and substances which retard evaporation; and (d) top-notes which are usually low-boiling, fresh-smelling materials.

In yet another method of using $OBP_L$, the protein is covalently attached to a chromatographic column packing material, for example, cellulose or agarose beads. A crude mixture of compounds can be added to such a column packing material, and odorants are preferentially retained upon the column. The odorants can then be isolated, by specific elution from the chromatographic column material. Differential elutions from the chromatographic column also provide a means of separating one odorant from another. Such column chromatographic methods are well known in the art as well as methods of elution and differential elution.

Because $OBP_L$ does bind odorants, it will have the effect of reducing the rate of volatilization of odorants from solutions and perfumed products. Thus, use of $OBP_L$ can prolong the effective shelf life of volatile odorant components in solutions and perfumed products. $OBP_L$ will be mixed with such a solution or product in an amount which is volatilization-reducing. Once again, such amounts can be readily determined according to routine tests for measuring volatilization in the art. Perfumed articles generally comprise aqueous and non-aqueous media, such as detergents, fabric softeners, cosmetic powders, creams and lotions, colognes, as well as other articles known in the art. Cosmetic lotions and creams include preparations for cleansing, softening, smoothing, and protecting the skin. Lotions often are liquids containing one or more insoluble substances. Both lotions and creams may be suspensions or emulsions.

Because of its role as a lipophilic molecule carrier in a hydrophilic environment, $OBP_L$ can also be used as a solubilizing agent. For example, a lipophilic odorant can be bound to $OBP_L$ and then the bound mixture can be further mixed with an aqueous medium to form an aqueous perfumed product or cologne. Thus, $OBP_L$ would increase the miscibility of lipophilic odorants in aqueous or semi-aqueous environments.

In still another method for using $OBP_L$, crude extracts of natural tissues can be screened for the presence of potent odorants. For example, a natural source, such as a fruit or vegetable, can be homogenized and extracted to form a crude extract. The crude extract can then be diluted over a broad range, for example, ten-fold dilutions over a range of six orders of magnitude. Each dilution can then be tested for its ability to displace the binding of a known strong odorant, for example, galbazine (IBMP), from $OBP_L$. For example, the strong odorant would be pre-bound to the $OBP_L$ and preferably labeled to facilitate measurement. Any extract which is able to displace the strong odorant at a high dilution indicates the presence in the natural tissue source of a potent odorant.

The following examples are given to more clearly and specifically present the foregoing general description. The invention is not limited by the scope of the examples, but only by the claims which are appended further below.

EXAMPLE 1

This example describes the cloning of the $OBP_L$ gene.

Purified rat $OBP_L$ was obtained using DEAE-cellulose chromatography and reverse phase HPLC, using the binding of tritiated odorants as an assay. See Pevsner et al, Proceedings of the National Academy of Sciences U.S.A. Vol. 82, Page 3050, 1985, and Vol. 83, Page 49-42, 1986. Direct N-terminal amino acid sequencing of the HPLC purified protein yields the sequence H₂N-ala-his-glu-asn-leu-asp-ile-ser-pro-ser-glu-val-asn-gly-asp. Based on the frequency of codon utilization, we constructed a mixed oligonucleotide probe (21 mer) containing thirty-two distinct sequences. This probes corresponded to the seven N-terminal amino acids:

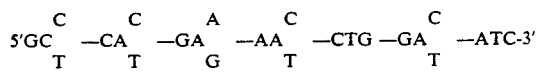

A cDNA library in Lambda gt10 was prepared from male rat nasal epithelium containing lateral nasal gland, by the method of Gubler and Hoffman (Gene, Vol. 25, Page 263, 1983) and 80,000 recombinant clones were screened using the [³²P]-labeled oligonucleotide probes. Sixteen independent clones were isolated. The complete sequence was determined for three of these clones (see FIGS. 1A-C). Hybridization-positive phage were subcloned in the plasmid vector Bluescript ™ (Strategene San Diego, Calif.) and sequenced by the Sanger random chain termination method (Proceedings of the National Academy of Sciences U.S.A. Vol. 74, Page 5463, 1977.)

The three full length clones which have been obtained (i.e., that encode the full protein as it is isolated from rat tissue,) are clone 8F3 (801 base pairs), clone 850 (782 base pairs), and clone 800 (760 base pairs). All three clones have a 3' end at nucleotide number 801, but their 5' ends vary. Clone 8F3 begins at nucleotide number 1 in FIG. 1A. Clone 850 begins at nucleotide number 19, and clone 800 at nucleotide number 41. The coding sequence for the native protein as it is isolated from rat begins at nucleotide 62.

We detect a long open reading frame predicted to encode 172 amino acids. The predicted initiating methionine is followed by fourteen hydrophobic amino acids. The residues immediately following this presumed leader sequence correspond to the N-terminal protein sequence. Eight amino acids of the N-terminus determined by amino acid analysis were not encoded in the oligonucleotide probe. The fact that these eight amino acids in the cDNA correspond exactly to the sequence determined from amino acid analysis, confirms that the isolated cDNA indeed encodes $OBP_L$. The putative ATG start code at position 17 is surrounded by a consensus sequence typical of eukaryotic ribosomal start sites (Kozak, Nucleic Acids Research Vol. 12, Page 857, 1984,) and is indicated as boxed nucleotides in FIGS. 1A-C. The amino acids which were determined from the protein sequencing are underlined in FIGS. 1A-C.

Features of the determined sequence indicating that a full length cDNA clone has been isolated include: (1) a characteristic ribosome binding sequence at the putative initiating methionine; (2) a polyadenylation signal at nucleotides 737 to 742; (3) a poly(A) sequence at the 3' end. Sequence analysis of a second clone reveals three, single-nucleotide substitutions compared to the first cloned sequence. All of these nucleotide changes occur in the 3' untranslated region. In FIGS. 1A-C these variations are indicated above the main line of sequence and marked with an asterisk. Bam HI, Taq I and Hinc II restriction sites are indicated by lines above the nucleotide sequence. The Hinc II site is present in clone 800 (the "variant" clone) but not in clones 850 or 8F3. The termination codon TAA is at position 553. The polyadenylation signal AATAAA is underlined. Both strands of clones 850 and 800 were completely sequenced. Clone 850 and 800 begin at positions 19 and 41 of clone 8F3, respectively.

Subclones of the larger cDNA clone from Lambda gt10 were recloned into Bluescript ™ phagemid's Eco RI site (obtained from Strategene Cloning Systems, San Diego, Calif.). Bluescript ™ contains the T3 and T7 promoters in the coding region of the lac Z gene, thus allowing the production of fusion proteins. Between the T3 and T7 promoters is a multiple cloning site containing the Eco RI (and other) restriction sites.

The ten subclones which have been constructed in the Bluescript ™ phagemid contain the 5' and 3' Bam HI fragments of clone 850, the 5' and 3' Bam HI fragments of clone 800, the 5' and 3' Taq I fragments of clone 850, and the 5' and 3' Taq I fragments of clone 800. In addition, 5' and 3' Hinc II fragments of clone 800 have been inserted into Bluescript ™ phagemid. The latter fragment contains no translated DNA sequences of $OBP_L$. All three of the large clones, 8F3, 850, and 800, contain all of the nucleotides which are necessary to code for the mature $OBP_L$ isolated from rat.

EXAMPLE 2

This example shows Northern blot analysis indicating the tissue distribution of the mRNA for $OBP_L$.

Total RNA was isolated from twelve tissues in the presence of guanidinium isothiocyanate as described in Thomas, Proceedings of the National Academy of Sciences U.S.A., Vol. 77, p. 5201, 1980. RNA (15 ug per lane) was treated with glyoxal and subjected to electrophoresis on a 1% agarose gel in 10 mM sodium phosphate buffer (pH 7.0). RNA was transferred to Nytran ™ (Schleicher & Schuell) and hybridized to [³²P]-labeled clone 850 (specific activity $6 \times 10^8$ dpm/ug) by random primer labeling. The filter was hybridized for twelve hours at 42° C., washed twice for twenty minutes 0.3M NaCl/30 mM sodium phosphate/0.5% SDS at 22° C., washed for twenty minutes in 75 mM NaCl/7.5 mM sodium phosphate/0.5% SDS at 42° C., air dried, and autoradiographed. Molecular sizes were determined from a one kilobase ladder (obtained from BRL, Bethesda, Md.) subjected to electrophoresis in adjacent lanes.

The tissues which were tested for the presence of hybridizing RNA were olfactory epithelium, lateral olfactory epithelium including the lateral nasal glands, nasal respiratory epithelium, and olfactory bulb. Detectable signal was apparent only in nasal tissues, indicating that mRNA for $OBP_L$ is restricted to the nose. The abundance of OBP message is comparable in respiratory and olfactory epithelium. However, the highest level of message are detected in the region of the lateral nasal gland (LNG), also known as Steno's gland. Microscopic localization of $OBP_L$ mRNA by in situ hybridization reveals a highly selective localization of $OBP_L$ message to the LNG.

The $OBP_L$ mRNA observed in olfactory and respiratory epithelium might reflect contaminating LNG tissue. The size of the OBP message is about one kilobase, which is 200 nucleotide longer than the size of the cloned cDNA. The significance of the slightly higher molecular weight of the message in the respiratory epithelium compared to the LNG and the olfactory epithelium is not clear, but may reflect a differential extent of polyadenylation.

EXAMPLE 3

This example shows a Southern analysis of rat genomic DNA using an $OBP_L$ probe.

Genomic DNA was isolated from rat liver and digested for ten hours at 37° C. with Hinc II (lanes 2 and 4 or BamH I (lanes 1 and 3.) See FIGS. 3A & B. Fifteen ug of DNA per lane were subjected to electrophoresis on a 1% agarose gel and transferred to Nytran ™. Clone 800 was digested with Hinc II to generate a 5' fragment (corresponding to nucleotides 41 to 570 of clone 8F3). Genomic DNA blots were hybridized for twelve hours at 65° C. to [$^{32}$P]-labeled clone 800 (in panel a) or the 5' cDNA fragment (in panel B). Filters were washed twice for fifteen minutes in 0.3M NaCl/30 mM sodium phosphate/0.1% SDS at room temperature; then washed for ten minutes in 75 mM NaCl/7.5 mM sodium phosphate/0.1% SDS at 65° C., air dried, and autoradiographed. Molecular sizes were determined from lambda/Hind III markers (obtained from BRL) subjected to electrophoresis in adjacent lanes.

The results suggest a limited family size of about two to four members. Because of the differences between the two $OBP_L$ cDNA clones in the 3' untranslated region, it was thought that at least two genes would be in the $OBP_L$ family. These results show that microheterogeneity in the $OBP_L$ protein is not responsible for the ability of $OBP_L$ to bind odorants of widely varying chemical structures. Such a microheterogeneity among an apparently homogeneous $OBP_L$ was formally possible before these results were obtained.

EXAMPLE 4

The sequence of $OBP_L$ obtained from the cDNA clones was compared by computer to other sequenced proteins. A similarity was revealed between $OBP_L$ and a group of proteins with similar properties. See Table 1, and FIG. 4. See Pervaiz et al., Science, Vol. 228, p. 335, 1985; and FASEB Journal, Vol. 1, p. 209, 1987; and Sawyer, Nature, Vol. 327, p. 659, 1987.

Homologies within the family of proteins related to $OBP_L$ occur at several sites which are indicated by the shaded areas in FIG. 4. Two consensus sequences are apparent, beginning at amino acid residues 12 and 89 of mature $OBP_L$. The first is basic-hyd-X-gly-X-trp-aro-X-hyd where basic is arg or lys, hyd is a hydrophobic residue (ile, leu, met, phe, tyr), aro is aromatic (phe or tyr) and X is any residue. The second consensus sequence is aro-X-hyd-hyd-X-thr-asp-tyr-asp-X-aro-hyd-hyd. The hyd-X-gly-X-trp consensus sequence also occurs near the N-terminus of a different family of ligand-binding proteins of which retinol-binding protein is a member. Other family members include cellular retinoic binding proteins I and II, cellular retinoic acid binding protein, peripheral nerve myelin P2 protein, heart and instestinal fatty acids binding protein, and murine adipocyte protein P422. We suggest that these two families are evolutionarily related.

The structures of retinol-binding protein, beta lactoglobulin, and insecticyanin have been determined by X-ray crystallography at high resolution. These three proteins share a remarkably similar structure containing an eight-stranded antiparallel beta-barrel motif that forms the core of the molecule. The first consensus sequence (containing gly-X-trp) occurs near the end of the first beta-barrel, while the second sequence (containing thr-asp-tyr) occurs near the sixth beta-sheet. None of the amino acids in the consensus sequences is in contact with the bound ligand.

Initial alignments were made using the DFASTP program of Lipman and Pearson, Science, Vol. 227, p. 1435, 1985, on a VAX/VMS computer; final alignment was manual. Abbreviations and sources of protein sequence data which are used in FIG. 4 are: alpha $2M = alpha_2$ microglobulin (Unterman et al., Proceedings of the National Academy of Sciences U.S.A., Vol. 78, p. 3478, 1981); BBLG=Bovine beta-lactoglobulin, (Preaux et al. Hoppe-Seyler's Z. Physiol. Chem., Vol. 360, p. 1595, 1979); BG=protein BG of Bowman's glands, (Lee et al., supra); HC=protein of heterogeneous charge (Takagi, Biochemistry and Biophysics Research Communications, Vol. 98, p. 997, 1981, and Lopez et al., Biochemistry and Biophysics Research Communications, Vol. 103, p. 919, 1981); AGP=Alpha$_1$-acid glycoprotein (Ricca et al., Journal of Biological Chemistry, Vol. 256, Page 11199, 1981); APOD- =apolipoprotein D, (Drayna et al., Journal of Biological Chemistry, Vol. 261, p. 16535, 1986); Thi=Tobacco Hornworm Insecticyanin (Riley et al., Journal of Biological Chemistry, Vol. 259, p. 13159, 1984); RBP=Retinol Binding Protein (Colantuoni et al., Nucleic Acids Research, Vol. 22, p. 7769, 1988 and Pervaiz et al., FASEB Journal, Vol. 1, Page 209, 1987); Purp- =Purpurin (Burman et al., Cell, Vol. 51, p. 135, 1987). The amino acid residues in FIG. 4 are shaded where seven or more residues in a column are either identical, acidic, basic, aromatic, or hydrophobic.

EXAMPLE 5

This example demonstrates the localization of $OBP_L$ mRNA to coronal sections of rat nasal epithelium.

Two RNA probes were produced by transcription from a rat $OBP_L$ cDNA template. The cDNA containing 760 nucleotides including all of mature $OBP_L$ as well as part of its predicted hydrophobic leader sequence and a 3' untranslated region was subcloned in the plasmid vector pGEM-2 (Promega Biotech, Madison, Wis.). Run-off complimentary RNA (cRNA) transcripts were generated using the SP6 polymerase to form antisense probes (complimentary to mRNA) or using the T7 polymerase to form sense probes (identical to mRNA). The cDNAs were made according to the protocol of Promega Biotech using the restriction enzymes in Hind III and Sph I to yield run-off transcripts of 860 (antisense) and 1300 (sense) nucleotides. Transcripts were labeled with [$^{35}$S]-CTP to a final specific activity of 1,250 Ci/mmol.

The in situ procedure was modified from the method of Uhl. In Situ Hybridization in Brain, Plenum, N.Y., 1986. Male rats (200 grams, Sprague Dawley) were perfused with 0.1% paraformaldehyde in phosphate-buffered saline (PBS) and whole nasal epithelium was embedded in Tissue-tek ™ (Miles Laboratories, Naperville, Ill.). The tissue was rapidly frozen and 10 um coronal sections were cut on a cryostat at $-20°$ C. Sections were post-fixed for five minutes in 4% paraformaldehyde in PBS, rinsed twice in sterile PBS, incubated for ten minutes at 23° C. in 0.25% acetic anhydride/0.1M triethanolamine/0.9% NaCl and then dehydrated through a graded series of ethanol (70%, 80%, 95%, 100%), chloroform (100%), ethanol (100%, 95%).

Sections were then incubated with antisense or sense labeled cRNA probes (1 × 10⁶ cpm per section) at 38° C. for 18 to 24 hours. After hybridization, sections were washed four times for fifteen minutes in 1X SSC (150 mM NaCl/15 mM sodium citrate) at 55° C. To confirm the hybridization specificity, antisense cRNA was coincubated with 1700-fold excess unlabeled cRNA. Additional sections were post-hybridized with RNase A (12.5 ug/ml 22° C., 10 minutes).

In situ hybridization reveals a striking density of the labeled cRNA for $OBP_L$ in the LNG. See FIG. 5A. Hybridization of the antisense probe to tissue sections results in a high density of silver grains over the LNG. This labeling is specific for $OBP_L$ mRNA, since incubation with the sense probe produces virtually no silver grains, see FIG. 5B. The specificity of labeling of $OBP_L$ mRNA is further substantiated by the elimination of silver grains with excess unlabeled probe. A similar pattern of localization is observed when silver grains are visualized with emulsion-coated covered slips.

EXAMPLE 6

This example demonstrates localization of $OBP_L$ by immunohistochemistry.

$OBP_L$ was purified from adult rat olfactory epithelium using tritiated odorant binding as an assay. Antibodies were raised in rabbits by standard techniques. Cryostat tissue sections were prepared as described above except that rats were perfused in 1% glutaraldehyde. Sections were immunohistochemically stained using an avidin/biotin/peroxidase technique (Vector Laboratories) using diaminobenzidine and hydrogen peroxide as substrates. Tissue sections were incubated with a 1:12,000 dilution of antiserum against rat $OBP_L$ or preimmune serum for 48 hours at 4° C.

Immunohistochemical staining with this antiserum reveals a selective localization of $OBP_L$ in the rat to the LNG (see FIG. 5C). No staining is apparent with preimmune serum. (See FIG. 5D)

EXAMPLE 7

This example demonstrates the specificity of an antibody raised against $OBP_L$.

Figure 6:
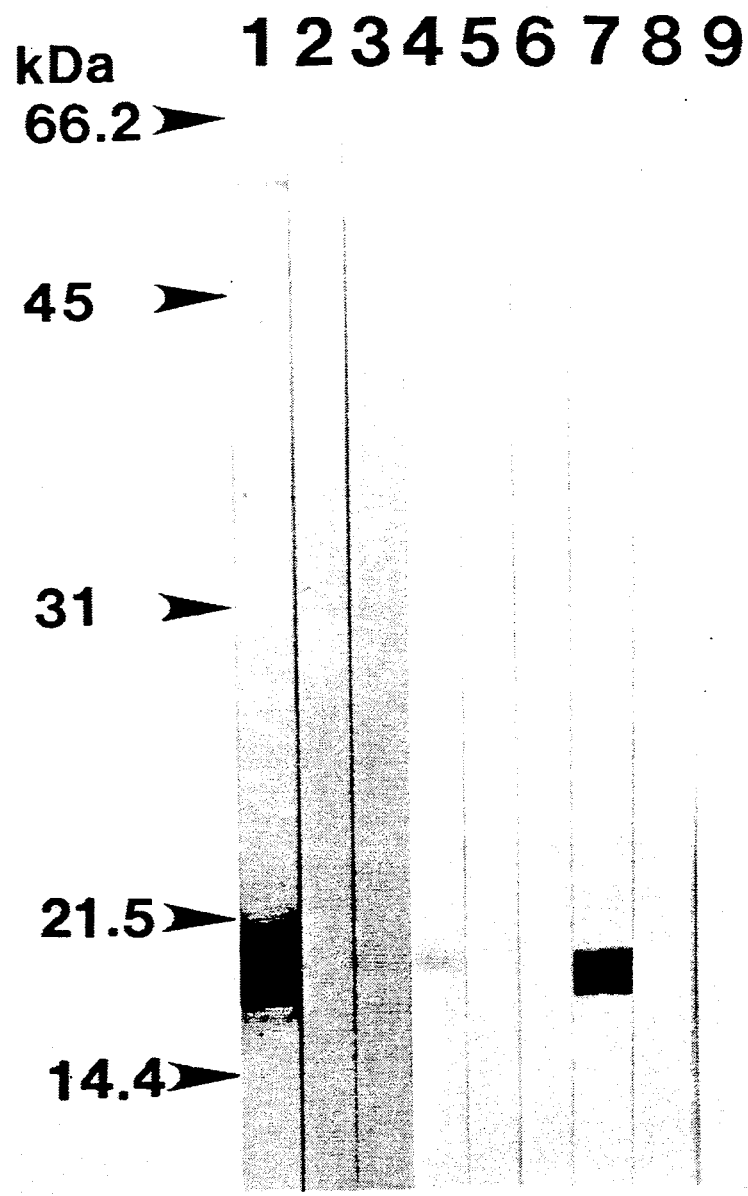
FIG. 6 shows a Western blot analysis of rat and cow nasal homogenates with anti-$OBP_L$ antiserum.

We have raised polyclonal antibodies to $OBP_L$. Western blot analysis of rat nasal homogenates reveals that this antiserum recognizes a doublet with subunit molecular weight of about 20 kDa, corresponding to the molecular size of mature $OBP_L$. See FIG. 6. No $OBP_L$ immunoreactivity is apparent in bovine nasal homogenates, indicating a lack of immunological cross-reactivity between bovine OBP and rat $OBP_L$.

EXAMPLE 8

This example demonstrates the localization of odorant binding activity by tritated odorant autoradiography.

Twenty day old male rats were perfused with 0.4% paraformaldehyde. Tissues were embedded in 50% brain paste/50% Tissue-Tek ™, rapidly frozen at −20° C., and 8 um cryostat tissue sections were cut and dessicated on slides for twelve hours. Slides were preincubated for five minutes in 30 mM Tris-HCl (pH 7.4) then incubated for 90 minutes at room temperature in 100 mM tritiated IBMP, tritiated amylacetate, or tritiated isovaleric acid, or in 200 nM tritiated DMO. Nonspecific binding was determined by co-incubation of the radioactive odorant with 500 uM unlabeled IBMP, amylacetate or isovaleric acid or with 50 uM DMO. After incubation, slides were rinsed in 30 mM Tris-HCl (30 seconds), washed twice for one minute in water, dried, dessicated for twelve hours and then exposed to Ultrafilm ™ (Kodak) for three weeks at −20° C.

We have localized $OBP_L$ in rat nasal tissue by autoradiography utilizing tritiated odorants. See FIG. 5E. Autoradiographic grains are displaced by an excess of unlabeled odorants, indicating that the binding is saturable. See FIG. 5F. The bound tritiated odorants are confined to the LNG with a pattern essentially the same as that observed by $OBP_L$ immunohistochemistry and in situ hybridization. We have observed saturable autoradiographic patterns with the odorants IBMP, DMO, and amylacetate which all bind to purified bovine OBP and rat $OBP_L$. Tritiated isovaleric acid, which fails to bind bovine OBP or rat $OBP_L$, also fails to specifically label the nasal epithelium autoradiographically. This further confirms the specificity of the odorant autoradiography for OBP.

We claim:

1. A method of isolating an odorant-binding protein gene comprising:
   preparing cDNA using an mRNA template isolated from lateral nasal gland tissue;
   inserting the cDNA into DNA vectors to form recombinant DNA molecules;
   transforming host cells with said recombinant DNA molecules to form transformed cells; and
   detecting the presence of odorant-binding protein DNA in said transformed cells.

2. The method of claim 1 wherein said detecting of odorant-binding protein DNA is accomplished by hybridization of a nucleic acid probe to the DNA of said transformed cells, said probe containing sequences which, when translated, produce the amino acid sequence of an odorant-binding protein.

3. The method of claim 1 wherein detecting the odorant-binding protein DNA is accomplished by hybridization to a nucleic acid probe which comprises a sequence of at least about twenty nucleotides from the sequence of the rat odorant-binding protein gene.

4. The method of claim 1 wherein detecting said odorant-binding protein DNA is accomplished by testing said transformed cells for the production of protein which is immunoreactive with anti-odorant-binding protein antibody.

5. The method of claim 1 wherein detecting said odorant binding DNA is accomplished by testing said transformed cells for the production of a protein which specifically binds odorant molecules.

6. A method of producing an odorant-binding protein, comprising:
   transforming host cells with a recombinant molecule comprising a gene for an $OBP_L$ which is positioned downstream from a transcriptional promoter and downstream from and in phase with a translational start site to form transformed cells;
   growing said transformed cells in a culture medium under conditions such that said transformed cells express the protein encoded by said odorant-binding protein gene; and
   harvesting the expressed protein encoded by said odorant-binding protein gene from said transformed cells and/or said growth medium.

* * * * *